(12) United States Patent
Todd et al.

(10) Patent No.: US 7,642,990 B2
(45) Date of Patent: Jan. 5, 2010

(54) METHOD AND DEVICE FOR GUIDING A USER'S HEAD DURING VISION TRAINING

(75) Inventors: David P. Todd, Wellington, FL (US); Bernhard Sabel, Berlin (DE)

(73) Assignee: NovaVision, Inc., Boca Raton, FL (US)

( * ) Notice: Subject to any disclaimer, the term of this patent is extended or adjusted under 35 U.S.C. 154(b) by 654 days.

(21) Appl. No.: 11/153,250

(22) Filed: Jun. 15, 2005

(65) Prior Publication Data

US 2006/0092377 A1 May 4, 2006

Related U.S. Application Data

(60) Provisional application No. 60/579,875, filed on Jun. 15, 2004.

(51) Int. Cl.
*G09G 5/00* (2006.01)
(52) U.S. Cl. .................................. 345/7; 345/8; 345/55
(58) Field of Classification Search .................. 345/7–8, 345/55
See application file for complete search history.

(56) References Cited

U.S. PATENT DOCUMENTS

| | | | |
|---|---|---|---|
| 1,463,847 A | 8/1923 | Schilling | |
| 2,213,484 A | 9/1940 | Briggs | 128/76.5 |
| 3,883,234 A | 5/1975 | Lynn et al. | 351/23 |
| 4,260,227 A | 4/1981 | Munnerlyn et al. | 351/24 |
| 4,408,846 A | 10/1983 | Balliet | 351/203 |
| 4,421,392 A | 12/1983 | Crick et al. | 351/224 |
| 4,429,961 A | 2/1984 | Sheingorn | 351/226 |
| 4,533,221 A | 8/1985 | Trachtman | 351/203 |
| 4,660,945 A | 4/1987 | Trachtman | 351/203 |
| 4,679,920 A | 7/1987 | Takashi et al. | 351/226 |
| 4,971,434 A | 11/1990 | Ball | 351/224 |
| 4,995,717 A | 2/1991 | Damato | 351/224 |
| 5,035,500 A | 7/1991 | Rorabaugh et al. | 351/226 |
| 5,050,982 A | 9/1991 | Meissner | 351/203 |

(Continued)

FOREIGN PATENT DOCUMENTS

DE 9305147 4/1994

(Continued)

OTHER PUBLICATIONS

Portable Tech/Emory Device Checks for Concussions, http://www.gatech.edu/news-room/release.php?id=554, Apr. 26, 2005.

(Continued)

*Primary Examiner*—Richard Hjerpe
*Assistant Examiner*—Leonid Shapiro
(74) *Attorney, Agent, or Firm*—Sunstein Kann Murphy & Timbers LLP

(57) ABSTRACT

A head-guide for diagnosing or training vision of a user and methods of user thereof are disclosed. The head-guide may include a head-support for orienting a head of the user, a display-support for orienting a display. The head-guide may also include a guide-support connected to the head-support and the display-support. The head-support and display-support may be pre-configured to fix the relative position of the head and the display and the display may present visual stimuli to diagnose or train the vision of the user.

43 Claims, 7 Drawing Sheets

U.S. PATENT DOCUMENTS

| | | | |
|---|---|---|---|
| 5,088,810 A | 2/1992 | Galanter et al. | 351/203 |
| 5,139,323 A | 8/1992 | Schillo | 351/45 |
| 5,147,284 A | 9/1992 | Federov et al. | 600/9 |
| 5,191,367 A | 3/1993 | Salibello et al. | 351/243 |
| 5,206,671 A | 4/1993 | Eydelman et al. | 351/203 |
| 5,241,332 A | 8/1993 | Farrell | 351/246 |
| 5,305,027 A | 4/1994 | Patterson | 351/44 |
| 5,321,445 A | 6/1994 | Fossetti | 351/203 |
| 5,325,136 A | 6/1994 | Salibello et al. | 351/243 |
| 5,363,154 A | 11/1994 | Galanter et al. | 351/203 |
| 5,455,643 A | 10/1995 | Ki-Ho | 351/203 |
| 5,534,953 A | 7/1996 | Schmielau | 351/203 |
| 5,539,481 A | 7/1996 | Vax | 351/203 |
| 5,539,482 A | 7/1996 | James et al. | 351/246 |
| 5,550,602 A | 8/1996 | Braeuning | 351/243 |
| 5,565,949 A | 10/1996 | Kasha, Jr. | 351/224 |
| 5,883,692 A | 3/1999 | Agonis et al. | 351/224 |
| 5,886,770 A | 3/1999 | Damato | 351/237 |
| 5,912,723 A | 6/1999 | Maddess | 351/246 |
| 5,946,075 A | 8/1999 | Horn | 351/246 |
| 5,991,085 A | 11/1999 | Rallison et al. | 359/630 |
| 6,062,687 A | 5/2000 | Lofgren-Nisser | 351/46 |
| 6,286,960 B1 * | 9/2001 | Tomita | 351/245 |
| 6,290,357 B1 | 9/2001 | Massengill et al. | 351/209 |
| 6,321,338 B1 | 11/2001 | Porras et al. | 713/201 |
| 6,359,601 B1 | 3/2002 | Maguire, Jr. | 345/7 |
| 6,364,486 B1 | 4/2002 | Ball et al. | 351/203 |
| 6,742,892 B2 | 4/2002 | Liberman | 351/203 |
| 6,386,706 B1 | 5/2002 | McClure et al. | 351/237 |
| 6,406,437 B1 | 6/2002 | Zur et al. | 600/558 |
| 6,431,708 B2 | 8/2002 | Krebs | 351/203 |
| 6,443,977 B1 | 9/2002 | Jaillet | 607/88 |
| 6,464,356 B1 | 10/2002 | Sabel et al. | 351/203 |
| 6,519,703 B1 | 2/2003 | Joyce | 713/201 |
| 6,540,355 B1 | 4/2003 | Couture | 351/203 |
| 6,578,966 B2 | 6/2003 | Fink et al. | 351/239 |
| 6,592,221 B1 | 7/2003 | Stregova | 351/203 |
| 6,656,131 B2 | 12/2003 | Alster et al. | 600/558 |
| 6,688,746 B2 | 2/2004 | Malov | 351/239 |
| 6,769,770 B2 | 8/2004 | Fink et al. | 351/239 |
| 6,990,377 B2 | 1/2006 | Gliner | 607/54 |
| 7,004,912 B2 | 2/2006 | Polat | 600/558 |
| 7,104,659 B2 | 9/2006 | Grier et al. | 359/614 |
| 7,220,000 B2 | 5/2007 | Alster et al. | 351/224 |
| 7,275,830 B2 | 10/2007 | Alster et al. | 351/223 |
| 7,309,128 B2 | 12/2007 | Cappo et al. | 351/224 |
| 2002/0024364 A1 | 2/2002 | Fink et al. | 351/237 |
| 2002/0047987 A1 | 4/2002 | Massengill et al. | 351/204 |
| 2002/0107960 A1 | 8/2002 | Wetherall et al. | 709/225 |
| 2002/0186179 A1 | 12/2002 | Knowles | 345/8 |
| 2003/0020873 A1 | 1/2003 | Fink et al. | 351/200 |
| 2003/0090439 A1 * | 5/2003 | Spitzer et al. | 345/8 |
| 2003/0156254 A1 | 8/2003 | Turovetsky | 351/203 |
| 2003/0214630 A1 | 11/2003 | Winterbotham | 351/203 |
| 2004/0012758 A1 | 1/2004 | Lin | 351/203 |
| 2004/0051848 A1 | 3/2004 | Gotze et al. | 351/203 |
| 2004/0075811 A1 | 4/2004 | Liberman | 351/203 |
| 2004/0100616 A1 | 5/2004 | Eremeev | 351/203 |
| 2004/0257528 A1 | 12/2004 | Miyake et al. | 351/203 |
| 2005/0001980 A1 | 1/2005 | Spector | 351/203 |
| 2005/0041208 A1 | 2/2005 | Winterbotham | 351/203 |
| 2005/0122477 A1 | 6/2005 | Alster et al. | 351/237 |
| 2005/0213033 A1 | 9/2005 | Sabel | 351/203 |
| 2005/0213034 A1 | 9/2005 | Nagayoshi | 351/203 |
| 2005/0213035 A1 | 9/2005 | Yoshimeki et al. | 351/203 |
| 2006/0092377 A1 | 5/2006 | Sabel et al. | 128/898 |
| 2006/0283466 A1 | 12/2006 | Sabel | 128/898 |
| 2006/0288258 A1 | 12/2006 | Lo et al. | 714/46 |
| 2006/0290885 A1 | 12/2006 | Covannon et al. | 351/212 |
| 2007/0038142 A1 | 2/2007 | Todd et al. | 600/558 |
| 2007/0121070 A1 | 5/2007 | Alster et al. | 351/224 |
| 2007/0171372 A1 | 7/2007 | Seal et al. | 351/245 |
| 2007/0182928 A1 | 8/2007 | Sabel | 351/224 |
| 2007/0216865 A1 | 9/2007 | Sabel et al. | 351/203 |
| 2008/0013047 A1 | 1/2008 | Todd et al. | 351/203 |
| 2008/0024724 A1 | 1/2008 | Todd | 351/222 |
| 2008/0077437 A1 | 3/2008 | Mehta et al. | 705/2 |

FOREIGN PATENT DOCUMENTS

| | | |
|---|---|---|
| DE | 10207839 | 9/2002 |
| EP | 115263 | 8/1984 |
| EP | 128783 | 12/1984 |
| EP | 135736 | 8/1985 |
| EP | 0 242 723 A1 | 10/1987 |
| EP | 0242723 | 10/1987 |
| EP | 0537945 A1 | 4/1993 |
| EP | 544631 | 6/1993 |
| EP | 689822 | 1/1996 |
| EP | 775464 | 5/1997 |
| EP | 830839 | 3/1998 |
| EP | 1186271 | 3/2002 |
| EP | 1236432 | 9/2002 |
| EP | 1236433 | 9/2002 |
| EP | 1384462 | 1/2004 |
| EP | 1402869 | 3/2004 |
| EP | 1403680 A1 | 3/2004 |
| GB | 1465561 | 2/1977 |
| WO | WO 8000405 | 3/1980 |
| WO | WO 8810088 | 12/1988 |
| WO | WO 9100553 | 1/1991 |
| WO | WO 9110393 | 7/1991 |
| WO | WO 9200037 | 1/1992 |
| WO | WO 9517227 | 6/1995 |
| WO | WO 9700653 | 1/1997 |
| WO | WO 9811819 | 3/1998 |
| WO | WO 9849992 | 11/1998 |
| WO | WO 9952419 | 10/1999 |
| WO | WO 9959461 | 11/1999 |
| WO | WO 0012042 | 3/2000 |
| WO | WO 0036971 | 6/2000 |
| WO | WO 0113859 | 3/2001 |
| WO | WO 0145630 | 6/2001 |
| WO | WO 0147463 | 7/2001 |
| WO | WO 0180808 | 11/2001 |
| WO | WO 0209578 | 2/2002 |
| WO | WO 02/39754 | 5/2002 |
| WO | WO 0239754 | 5/2002 |
| WO | WO 2006002070 | 5/2002 |
| WO | WO 02053072 | 7/2002 |
| WO | WO 03002070 | 1/2003 |
| WO | WO 03002190 | 1/2003 |
| WO | WO 03007944 | 1/2003 |
| WO | WO 03020195 | 3/2003 |
| WO | WO 03041630 | 5/2003 |
| WO | WO 03/065964 A1 * | 8/2003 |
| WO | WO 03065964 | 8/2003 |
| WO | WO 03092482 | 11/2003 |
| WO | WO 03092570 | 11/2003 |
| WO | WO 03098529 | 11/2003 |
| WO | WO 2004066900 | 8/2004 |
| WO | WO 2005004985 | 1/2005 |
| WO | WO 2005037177 | 4/2005 |
| WO | WO 2005044096 | 5/2005 |
| WO | WO 2005063153 | 7/2005 |
| WO | WO 2005092270 | 10/2005 |
| WO | WO 2005110326 | 11/2005 |
| WO | WO 2005122872 | 12/2005 |
| WO | WO 2006006563 | 1/2006 |
| WO | WO 2007/003902 | 1/2007 |
| WO | WO 2007/109724 | 9/2007 |
| WO | WO 2007109724 | 9/2007 |

| | | |
|---|---|---|
| WO | WO 2008/077440 | 7/2008 |

OTHER PUBLICATIONS

Erich Kasten et al., Computer-based training for the treatment of partial blindness, Nature Medicine, vol. 4, No. 9, p. 1083-1087, Sep. 1998.

Burkhard Pleger et al., Functional magnetic resonance imaging mirrors recovery of visual perception after repetitive tachistoscopic stimulation in patients with partial cortical blindness, Neuroscience Letters, vol. 335, p. 192-194, 2003.

Walter Widdig et al., Repetitive visual stimulation: A neuropsychological approach to the treatment of cortical blindness, NeuroRehabilitation, vol. 18, p. 227-237, 2003.

Robert Sekuler, Vision Loss in an Aging Society: A Multidisciplinary Perspective/Vision Rehabilitation: Assessment, Intervention and Outcomes/The Lighthouse Handbook on Vision; Aug. 1, 2001, Gerontologist 556, vol. 41, Issue 4; ISSN: 0016-9013, © 2001.

Erich Kasten, Dorothe A. Poggel, Bernhard A. Sabel, Computer Based Training Stimulus Detection Improves Color and Simple Pattern Recognition in the Defective Field of Hemianopic Subjects; Nov. 1, 2000, Journal of Cognitive Neuroscience 1001, ISSN: 0898-929X; vol. 12, Issue 6; © 2000.

Rewiring Your Gray Matter: The brain: You can trach an old brain new tricks. Neuroplasticity promises to give a whole new meaning to 'changing your mind'; Jan. 1, 2000, Newsweek 63; ISSN: 0028-9604; vol. 134, Issue 26, © 2000.

Teaching the brain to restore sight; Popular Mechanics, Jan. 18, 1999, Associated Press Newswires, © 1999.

Philip A. Schwartzkroin, Synaptic Plasticity: Molecular, Cellular, and Functional Aspects (book reviews); May 20, 1994, Science 1179; vol. 264, No. 5162, ISSN: 0036-8075; © 1994.

J. Zihl, et al., Restitution of visual function in patients with cerebral blindness; Zihl and von Cramon, J Neurol Neurosurg Psychiatry (1979).

J. Zihl, et al., Restitution of visual field in patients with damage to the geniculostriate visual pathway; Zihl and von Cramon, Human Neurobiology (1982).

E. Kasten, S. Wuest, B. Sabel, Journal of Clinical and Experimental Neuropsychology 1998, vol. 20, No. 5, pp. 581-598 "Residual Vision in Transition Zones in Patients with Cerebral Blindness".

F. Schmielau, Restitution of visual function in cases of brain damaged patients: Efficacy of localization specific sensory and sensomotoric rehabilitation procedures. In "Psychologie in der Neurologie" [Psychology in Neurology], P. Jacobi (editor). Berlin: Springer, 115-126(1989).

E. Kasten et al., Restoration of vision II: Residual functions and training-induced visual field enlargement in brain-damaged patients.

K.K. ball, et al., Journal of the Optical Society of America A, vol. 5, No. 12, pp. 2210-2219 "Age and Visual Search: Expanding the Useful Field of View", Dec. 1998.

E. Kasten, et al., Spatial Vision, vol. 10, No. 4, pp. 499-503. "Programs for Diagnosis and Therapy of Visual Field Deficits in Vision Rehabilitation", 1997.

E. Kasten, et al., Restorative Neurology and Neurology and Neuroscience, vol. 8, No. 3, pp. 113-127, "Visual Field Enlargement After Computer Training in Bran-damaged Patients Whit Homonymous Deficits: An Open Pilot Trial", Aug. 1995.

Alan Cowley, Alan Cowley, Perimetric Study of Field Defects in Monkeys After Cortical and Retinal Ablations, Quarterly Journal of Experimental Psychology, pp. 232-245, Dec. 18, 1967.

New Research on the Efficacy of NoveVision VRT Presented at 32nd Annual North American Neuro-Ophthalmology Society Meeting; Mar. 2, 2006, Business Wire © 2006.

Sharon Begley, Training the brain to see again; Sharon Begley, May 1, 2005, Saturday Evening Post, vol. 277; Issue 3; ISSN: 00489239; © 2005 Bell & Howell Information and Learning Company.

In-Sung Yoo, Advances in Medicine: New therapy gives hope to stroke victims; In-Sung Yoo, Mar. 1, 2005, The New Journal, © 2005, The New Journal.

Sharon Begley, Stroke patients have hope in sight; As part of the revolution in neurobiology, doctors are trying to train healthy brain cells to take over the visual function of neurons damaged by a stroke; Sharon Begley, Wall Street Journal, Feb. 4, 2005, The Globe and Mail.

John Dorschner, Stroke victims improve vision with computer therapy; John Dorschner, Knight Ridder Newspapers, Jul. 19, 2004, The Tallahassee Democrat, © 2004.

Sharon Begley, Survival of the Busiest—Parts of the Brain That Get Most Use Literally Expand And Rewire on Demand; Sharon Begley, Oct. 11, 2002, The Wall Street Journal, © 2002.

Patienteninformation Sehtherapie, Spectros, Nethera, http://www.teltra.org/cms/site/index.php?id=29, 2005.

Patienteninformation Sehtherapie, Otcb, Nethera, http://www.teltra.org/cms/site/index.php?id=11, 2005.

Spectros Technik/Ablauf, Nethera, Teltra, http://www.teltra.org/cms/site/index.php?id=77, 2005.

International Search Report & Written Opinion.

Authorized Officer, Laure Acquaviva, *The International Search Report and The Written Opinion of the International Searching Authority*, International Searching Authority, Jul. 12, 2005, 17 pages. International Application No.: PCT/US2005/021065.

The International Bueran of WIPO: Authorized Officer-Dorothee Mulhausen, *Notification Concerning Transmittal of Copy of International Preliminary Report on Patentability*, PCT/US2005/021065, dated Jan. 4, 2007, 9 pages.

* cited by examiner

METHOD AND DEVICE FOR GUIDING A USER'S HEAD DURING VISION TRAINING

PRIORITY CLAIM

This application claims priority to U.S. Provisional Application Ser. No. 60/579,875, entitled "Method and Device for Guiding a User's Head During Vision Training," filed Jun. 15, 2004, and which is hereby incorporated by reference in its entirety.

TECHNICAL FIELD

The present invention relates to systems and methods to provide vision training to subjects including patients with vision impairment. In particular, the invention is directed toward positioning users and a source of visual stimuli to simplify and insure quality of the delivery vision training.

BACKGROUND ART

Therapeutic vision training is directed toward improving the visual performance of patients with vision impairments by stimulating their vision systems using visual stimuli. For example, as documented in the international PCT application with application number PCT/EP98/05505 and publication number WO 00/12042, which is hereby incorporated by reference herein in its entirety, presenting visual stimuli to the areas of residual vision (i.e., transition zones) of a human's visual system may allow improvement in the user's vision. Such training may be carried out on a personal computer for home use, the training performed in sessions on a daily schedule for a set period of time (e.g., an hour).

The location and orientation of a user's head relative to a display, used to present visual stimuli, needs to be identified each time training is performed to properly stimulate the correct zones in a user's visual field. Previous training regimens relied upon a user fixing their gaze in a particular location. The natural tendency of persons to move after being in an unsupported, fixed position for a relatively long period of time may cause misalignment of the visual stimuli relative to a user's visual field. Such misalignment may limit the effectiveness of a training session. Even if a user attempts to fix their head's position relative to a display, identifying the proper position may be difficult, especially for individual users outside of a clinical setting. As well, the amount of time required to properly align the relative position of the display with a user's visual field can be substantial. The prior art does not disclose a method or device which assures proper positioning of a user's head and eyes in relation to a display for vision training.

SUMMARY OF THE INVENTION

An embodiment of the invention is directed toward a head-guide for diagnosing or training vision of a user. The head-guide includes a head-support for orienting a user's head, a display-support for orienting a display; and a guide-support connected to the head-support and the display-support. The head-support and display-support are pre-configured to fix the relative position of the head and the display. The display is capable of presenting visual stimuli to train the vision of the user. Head-guides may be configured to be easily transportable.

Head supports for use with embodiments of the invention may be configured to support the head of a user in a discrete number of preselected positions. The head supports may include a chin support or a head strap or both. The guide-support may include a base attached to the head-support and the display-support. The display-support may be configured to support a preselected portable computer, and, optionally, may include a display base for positioning the portable computer in any of a discrete number of preselected positions.

The head-support and display-support may be configured to present a selected range of fixation points to the user. As well, they may be configured to present optical stimuli to a zone within the intact visual field of the user and to a zone outside the intact visual field of the user, and to train vision in one of the two zones or in areas of residual vision, where there is only partial visual function.

Another embodiment of the invention is directed toward a device for diagnosing or training vision of a user. The device includes a head-guide and a CPU in communication with a display, the head guide configured to hold the display. The CPU generates visual stimuli presented by the display. The visual stimuli are generated based upon the pre-configuration of the display-support and the pre-configuration of the head-support. The CPU may be configured to generate the visual stimuli based upon a plurality of pre-configurations for at least one of the display-support and the head-support. The CPU may also be configured to generate visual stimuli for diagnosing a condition of vision of the user.

Other embodiments of the invention include head-guides that are configured for presenting visual stimuli on a display to therapeutically train the vision of the subject. The head-guide may also be configured for presenting visual stimuli on a display to train a user to compensate for impairment of vision.

In another embodiment of the invention, a method of training vision of a subject includes the steps of providing a head-guide having a head-support for orienting a subject's head, a display-support for orienting a display, and a guide-support connected to the head-support and the display-support; positioning the head of the subject relative to the display using the head-guide; and training the vision of the subject by presenting visual stimuli on the display. The training may be directed toward therapeutic training of the vision of the subject, or compensating for impaired vision in the subject. The method may also include the step of diagnosing a condition of vision of the subject based upon visual stimuli presented on the display before training the vision of the subject.

An alternate embodiment of the invention is directed toward an improved method of training vision of a subject. The method includes having the subject respond to a training session that is presented on a display associated with a computer system, the computer system running a training program, and the display being observed by the subject through a head-guide. The improvement in the method includes providing a head-guide having a display-support defining a physical location for the display, a viewing access region defining a fixed location for the subject's head from which the display may be viewed, and a guide-support attached to the display-support and viewing access region, the guide-support defining a fixed distance between the display-support and viewing access region; and fixing a position of the head of the subject relative to a display using the head-guide.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Some embodiments of the invention described herein are directed toward devices and methods to therapeutically train a subject to compensate for impairment of vision. Such embodiments may include the use of head-guides, some specific examples of which are described herein, that position the head of a subject relative to a display. The display presents visual stimuli that are viewed by the subject, the stimuli resulting in therapeutic training of the impaired vision of the subject.

Figure 1:
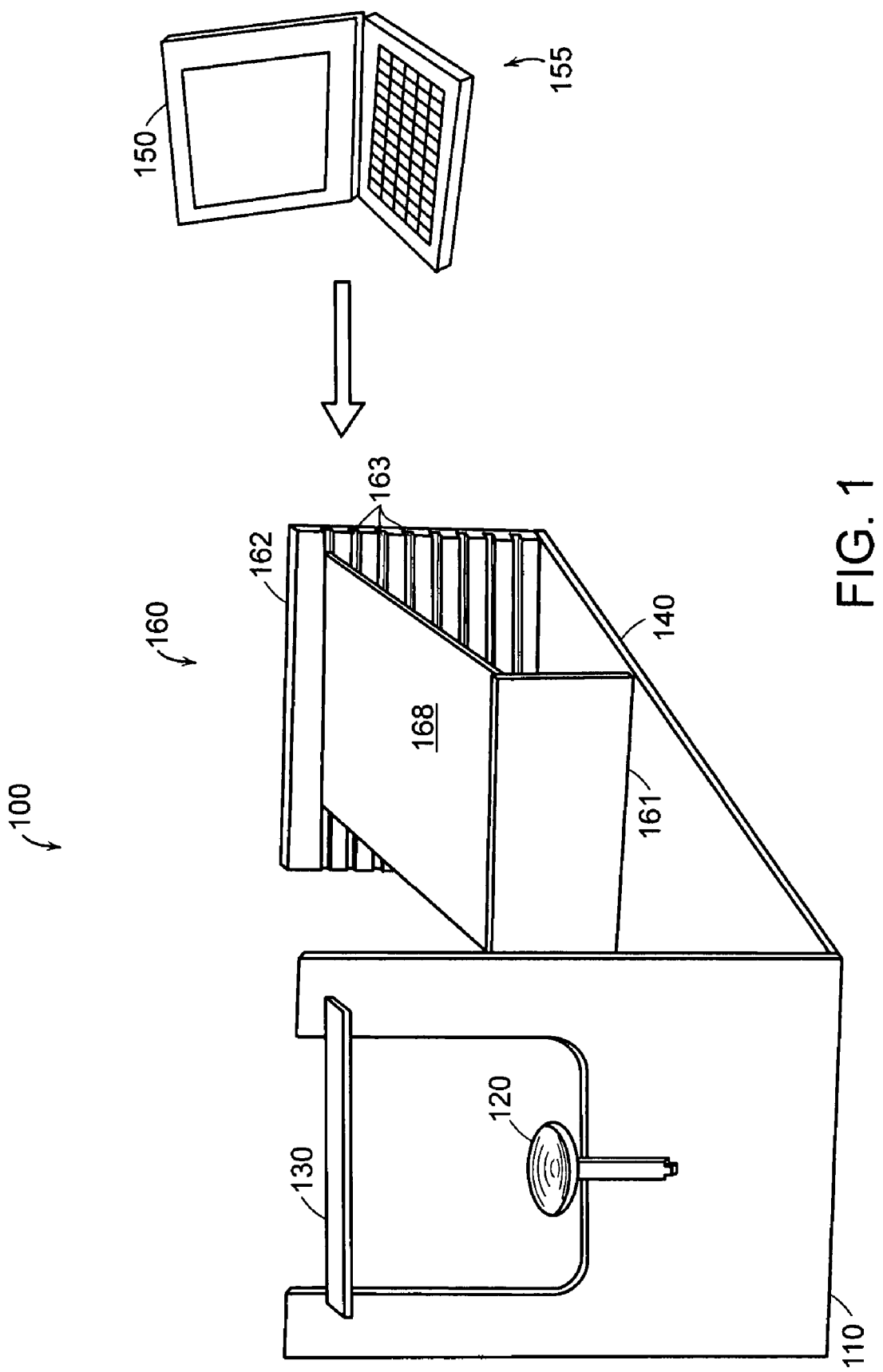
FIG. 1 depicts a perspective view of a head-guide with a portable computer to be supported by a display-support, consistent with an embodiment of the invention.

One particular embodiment of the invention is depicted in FIG. 1. A head-guide 100 is shown having a head-support 110 and a display-support 160, both of which are coupled to a guide-support in the form of a base 140. The head-support 110 orients the head of a user. The display-support 160 orients a display 150 used to present visual stimuli to the user for therapeutic vision training.

The head-support and display-support are preferably pre-configured to position the head of a user and the display (i.e., orienting the head and display, as well as fixing the distance of the head and display) such that the visual stimuli is properly presented to the user to impart the benefits of vision training. The display-support may be configured such that a display can be moved into various orientations guided by the display-support (e.g., the positioning of a portable computer). The visual stimuli presented by the display may also be determined to some extent by the specific configuration of the head-guide. For example, the physical and vision characteristics of the head of a user, and the characteristics of the display, are crucial in order to properly stimulate particular zones of a user's visual field (e.g., the "area of residual vision", or the "intact" zone).

Techniques of vision training are discussed in the international PCT application with application number PCT/EP02/01339 and publication number WO 03/065964 A1, the contents of which are hereby incorporated herein by reference in their entirety. Such techniques of training, and corresponding diagnostics, typically maintain the head of a user in relation to a display for an extended period of time. For example, during diagnostic testing, a diagnostic session typically is conducted over approximately a two-hour period in three-repetitions, each repetition lasting approximately 30 minutes with breaks. Likewise, a therapeutic session make last approximately 30 minutes, being conducted twice a day, six days a week. Thus, it is advantageous to utilize a head guide which supports the head of user to reduce the strain associated with maintaining a particular position for an extended period of time.

By pre-configuring the head-support and display-support of the head-guide, along with the visual stimuli to be presented by the display, the therapeutic benefits of vision training may be easily obtained on a transportable unit that a user may utilize from the home, or another desired location. Pre-configuration may simplify the set up associated with a vision training device, without the need for extensive calibration of the display and head-guide by the user. Furthermore, such pre-configuration may reduce the possibility of error in adjusting a display or head-guide, which could result in sub-optimal vision training. As well, given that the population of potential users of vision training includes a sizable fraction of persons with cognitive disabilities, the potentially increased ease-of-use and reliability associated with embodiments of the invention present attractive potential advantages over existing systems.

Returning to the embodiment of the invention shown in FIG. 1, the head-support supports a user's head in a particular orientation. The head-support 110 includes a chin support 120 and a head strap 130. The head-support is preferably constructed of a lightweight, strong material capable of supporting the weight of a user's head. For example, the head-support may be constructed of a transparent acrylic, or other lightweight polymer/composite material.

Figure 2:
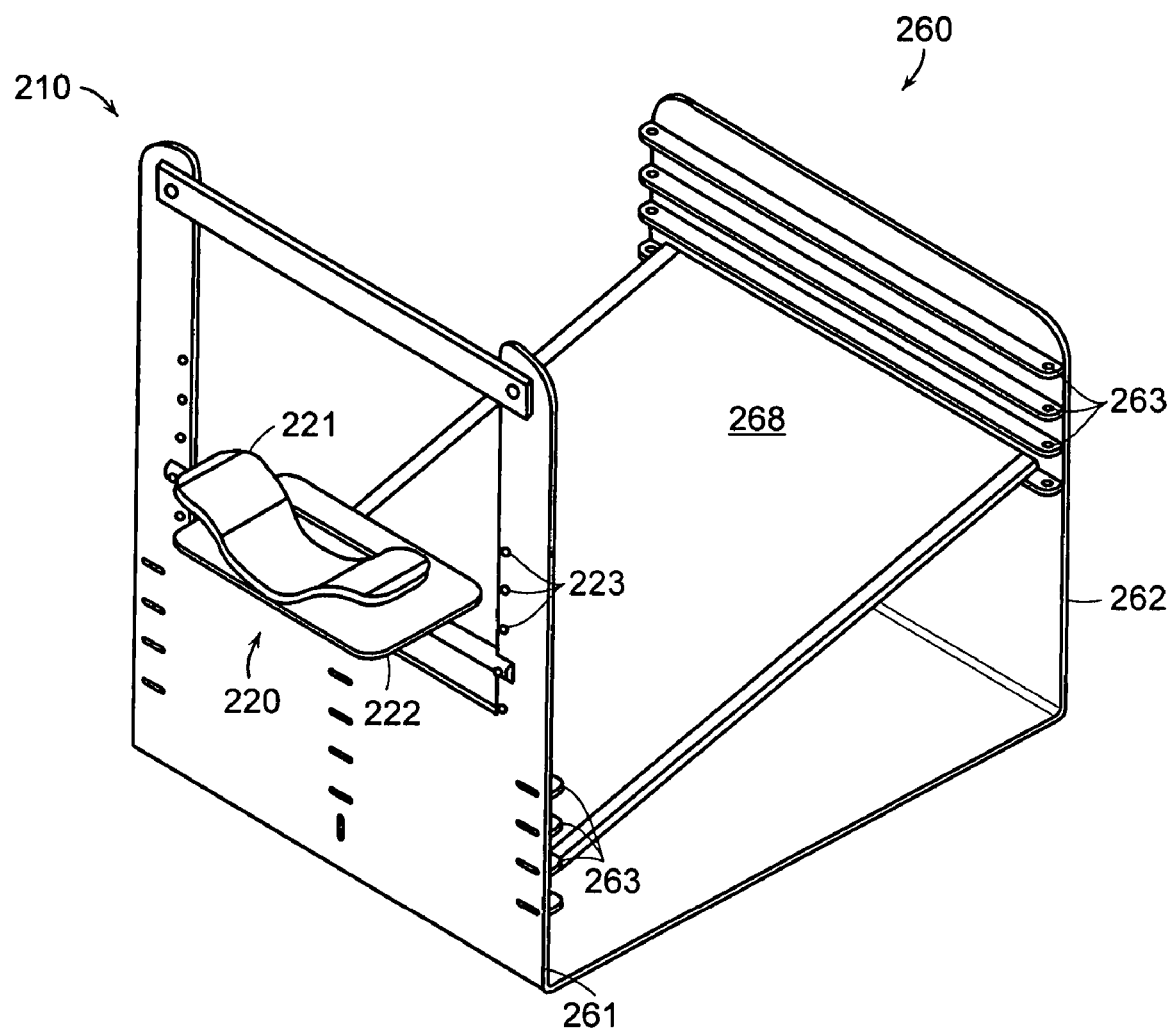
FIG. 2 depicts a perspective view of a head-guide with a discrete number of setting for a chin guide, and a deck for supporting a display, consistent with an embodiment of the invention.
Figure 3:
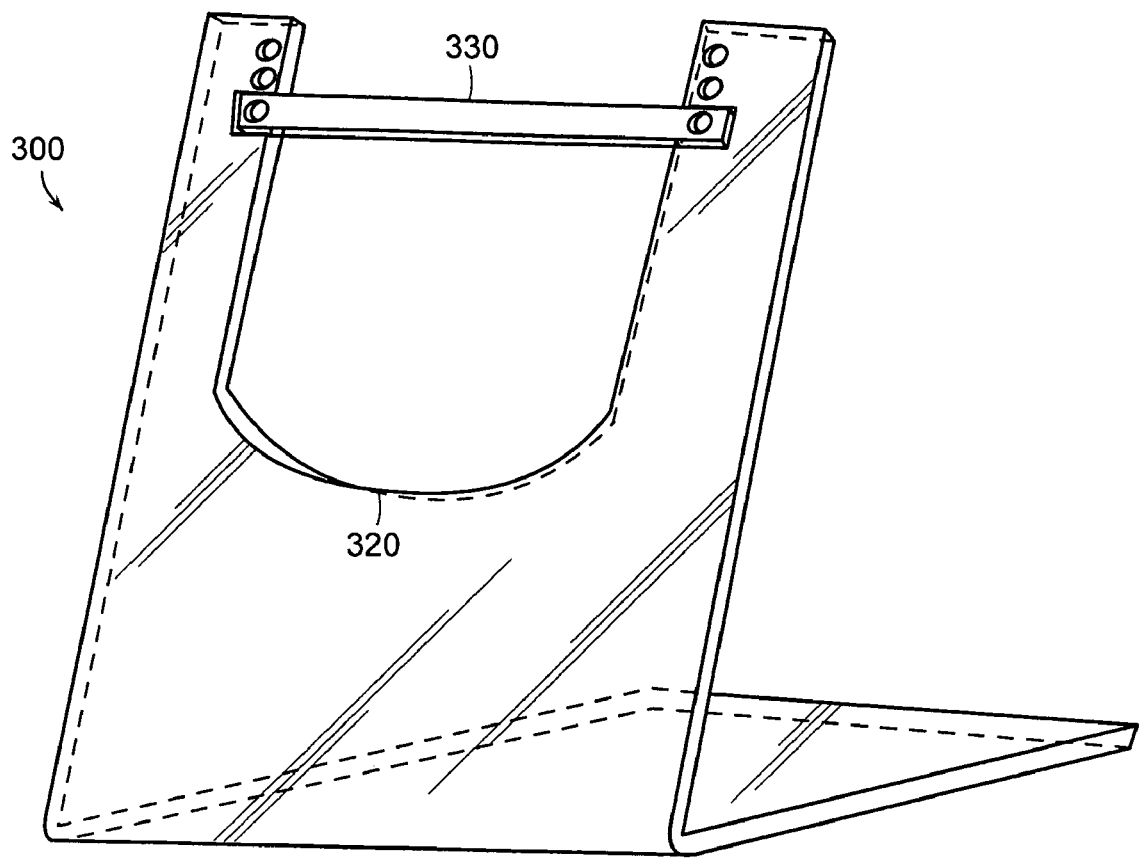
FIG. 3 depicts a perspective view of an embodiment of the invention that includes a head-support connected to a base.

The chin support is configured to allow a user's chin to contact the support comfortably, and to aid in positioning the head of the user. The chin support may be shaped and constructed in any manner that allows the support to function properly. For example, in FIG. 1, the chin support 120 has a separate stem and chin cushion. The cushion may be made of a soft material, such as silicone encased in a pliable cover, to make the chin support more comfortable to the user. In another example, as shown in FIG. 2, the chin support 220 includes a chin rest 221 coupled to a vertical adjustment piece 222, the latter piece being adjustable to pre-configured discrete settings 223. In yet another example, as depicted in FIG. 3, the chin support 320 may simply be a shaped portion of the head-support 300.

The head strap is configured to stabilize the head of a user in a comfortable manner. A head strap is preferably constructed of an elastic material capable of supporting the forehead of a user and returning to its original shape when the user's head is not in contact with the strap. Optionally, the strap may be a rigid material that is shaped with a curvature to accept the forehead of a user. The head-guide may also allow positioning of the head strap 330 in a number of pre-selected settings to conform to the user's comfort or to aid in positioning the head of a user, as shown in FIG. 3.

Though embodiments of the invention depicted in the Figures utilize a chin support and head strap as parts of a head-support, other structures that stabilize a head position without such elements are also consistent with a head-support.

The display-support is used to orient a display that presents visual stimuli to train the vision of the user. In the embodiments of the invention shown in the Figures, the display-support is configured to support a laptop computer. A display-support, however, is not limited in such a manner, and may be used to support any number of types of displays including, but not limited to, CRT screens and flat panel displays that may or may not be in an integral piece with a unit that generates the visual stimuli to be presented (e.g., a central processing unit (CPU)).

Display-supports may orient a display in a variety of manners. In one example, as depicted in FIGS. 1 and 2, a display-support 160, 260 includes deck-supports 161, 162, 261, 262 and a deck 168, 268. The deck-supports 161, 162, 261, 262 each include a discrete number of positions 163, 263 for supporting the deck 168, 268. The deck 168, 268 is inserted between the deck supports 161, 162 in a particular setting. A portable computer 155 with a display 150 rests on the deck 168. Note that in FIG. 2, the deck support 261 can also serve as a portion of the head-support 210. Deck-supports and the deck may take any form necessary to support a display; they are not limited to the embodiments shown in FIGS. 1 and 2. Optionally, a deck may include a marking to indicate precisely where on the deck that a display should be positioned.

The base 140, as shown in FIG. 1, is coupled to the head-support 110 and the display-support 160. The base fixes the relative distance between the head-support and the display-support, which ultimately impacts the visual stimuli emitted from the display and presented to a user. Though some embodiments of the invention shown in the Figures utilize a base, other guide structures may be utilized to connect the head-support and display-support. For example, a rigid elevated superstructure may suspend the head-support and display-support therefrom, with the head-support and display-support each being configured to contact a surface, such as a table; the whole assembly being self-supporting. As well, a guide-support may also have a discrete number of pre-configured settings to establish relative distances between a head-support and a display-support.

Figure 4:
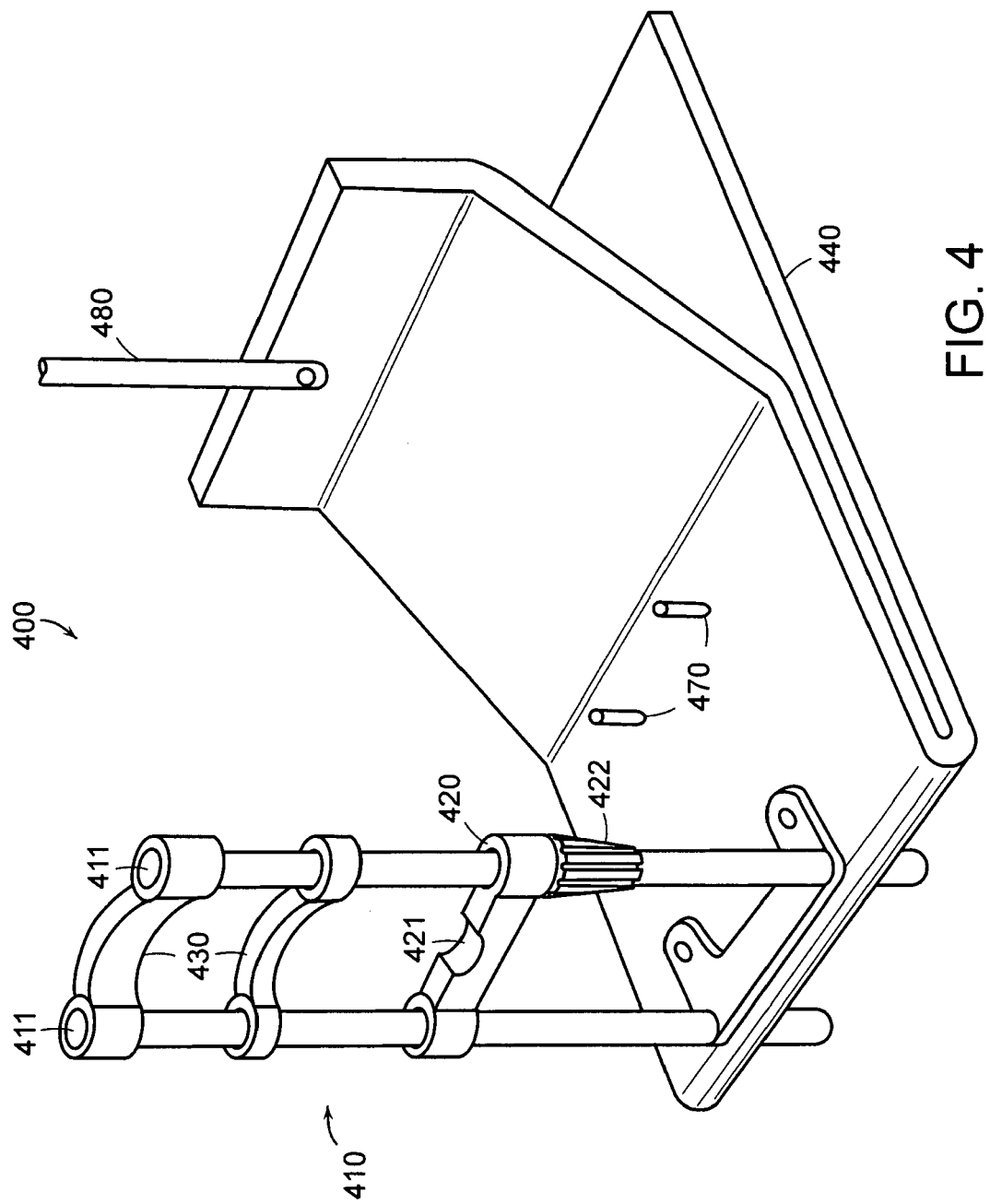
FIG. 4 depicts a perspective view of an embodiment of the invention of a head-guide which includes stop pins and a display stop to position the display of a portable computer.

FIG. 4 depicts another head-guide consistent with an embodiment of the invention. The head-support 410 of the head-guide 400 includes two posts 411 that are attached to the base. The chin support is a bar 420 across the two posts 411 that has a molded indentation 421 for supporting the chin of a user. The height adjuster 422 is used to designate the particular height of the chin support bar 420; such an adjuster may be used to manipulate the vertical height of a person's head relative to a display, and to accommodate people of differing height. In this particular embodiment of the invention, the vertical height of the chin support bar 420 may be adjusted to any height that may be accommodated by the two posts 411 and height adjuster 422. Markings, or other designators, may be labeled on the posts 411 to designate particular pre-configured positions for the chin support bar 420. Two head straps 430 are also used to support the head of a user. A rigid sheet of plastic 440, folded back upon itself and slanting upward in the vertical direction, acts as both a base and display-support. Stop pins 470 are utilized to position the bottom of a portable computer that includes a display. A display stop 480 acts to position the display at a preset angle.

Figure 5B:
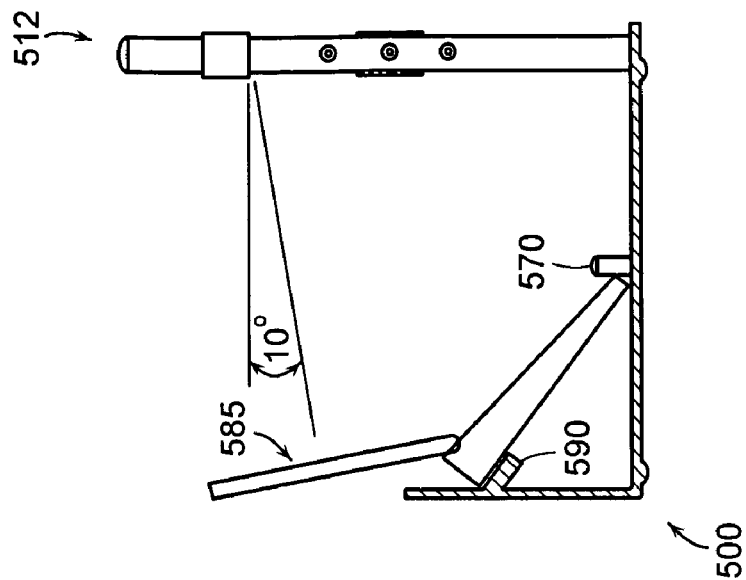
FIG. 5B depicts a side view of a head-guide with a portable computer mounted in the head-guide, consistent with an embodiment of the invention.
Figure 5A:
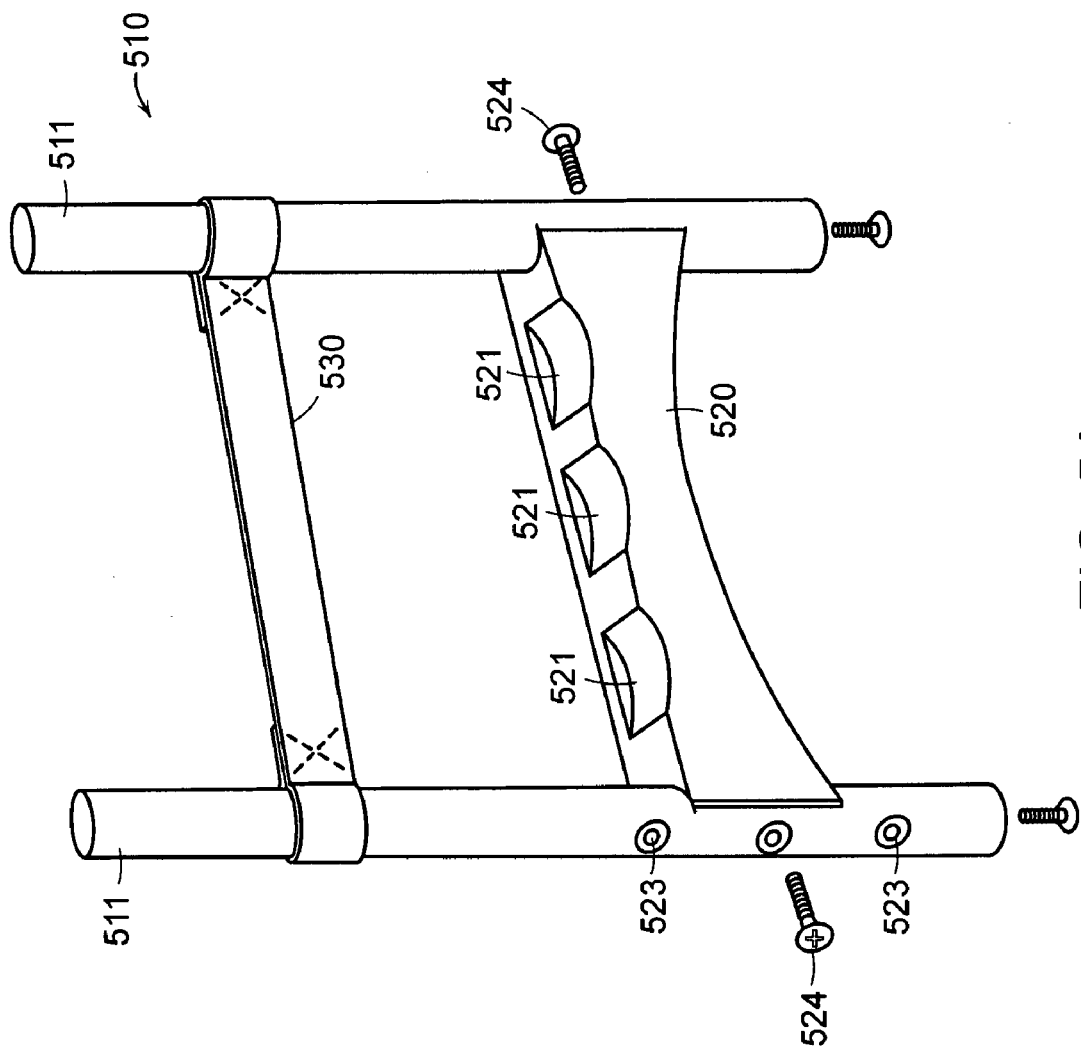
FIG. 5A depicts a perspective view of a head-support with multiple chin rests and multiple chin height positions for use with an embodiment of the invention.

FIGS. 5A and 5B depict related embodiments of the invention. FIG. 5A depicts another version of a head-support 510 that may be utilized in a head-guide. The head-support 510 is composed of two posts 511 that may be screwed into a base. The chin support bar 520 has a plurality of chin rest positions 521, allowing a number of positions for a user's chin to be placed in. As well, the chin support bar 520 may be positioned in one of three vertical heights 523, the bar being secured by screws 524. A head strap 530 is also placed between the two posts. The head strap 530 may be vertically adjusted to suit the head of a user.

FIG. 5B depicts a side view of the head-guide 500. The display-support includes back tabs 590 to support a portable computer 585. The tabs 590 and stops 570 are precisely positioned to locate and orient the display relative to the head of a user in the head-support 512. The tabs and stops may be positioned in alternative locations, with predrilled holes in the molded plastic sheet, to provide a particular orientation of the display relative to the user.

Figure 6:
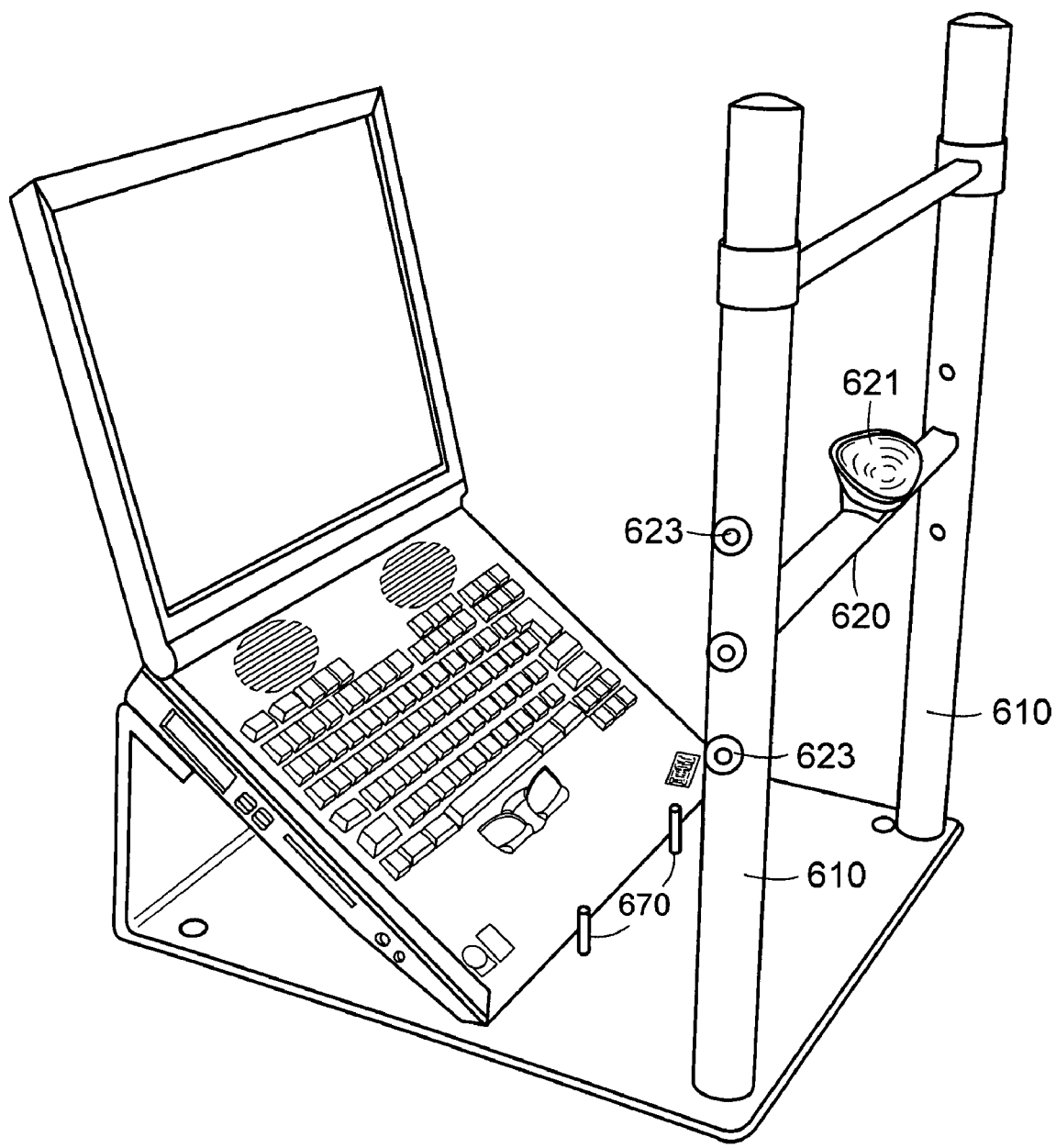
FIG. 6 depicts a perspective view of a head-guide with a portable computer mounted in the head-guide, the chin rest being an attached cup-shaped piece of the head-support, consistent with an embodiment of the invention.
Figure 7:
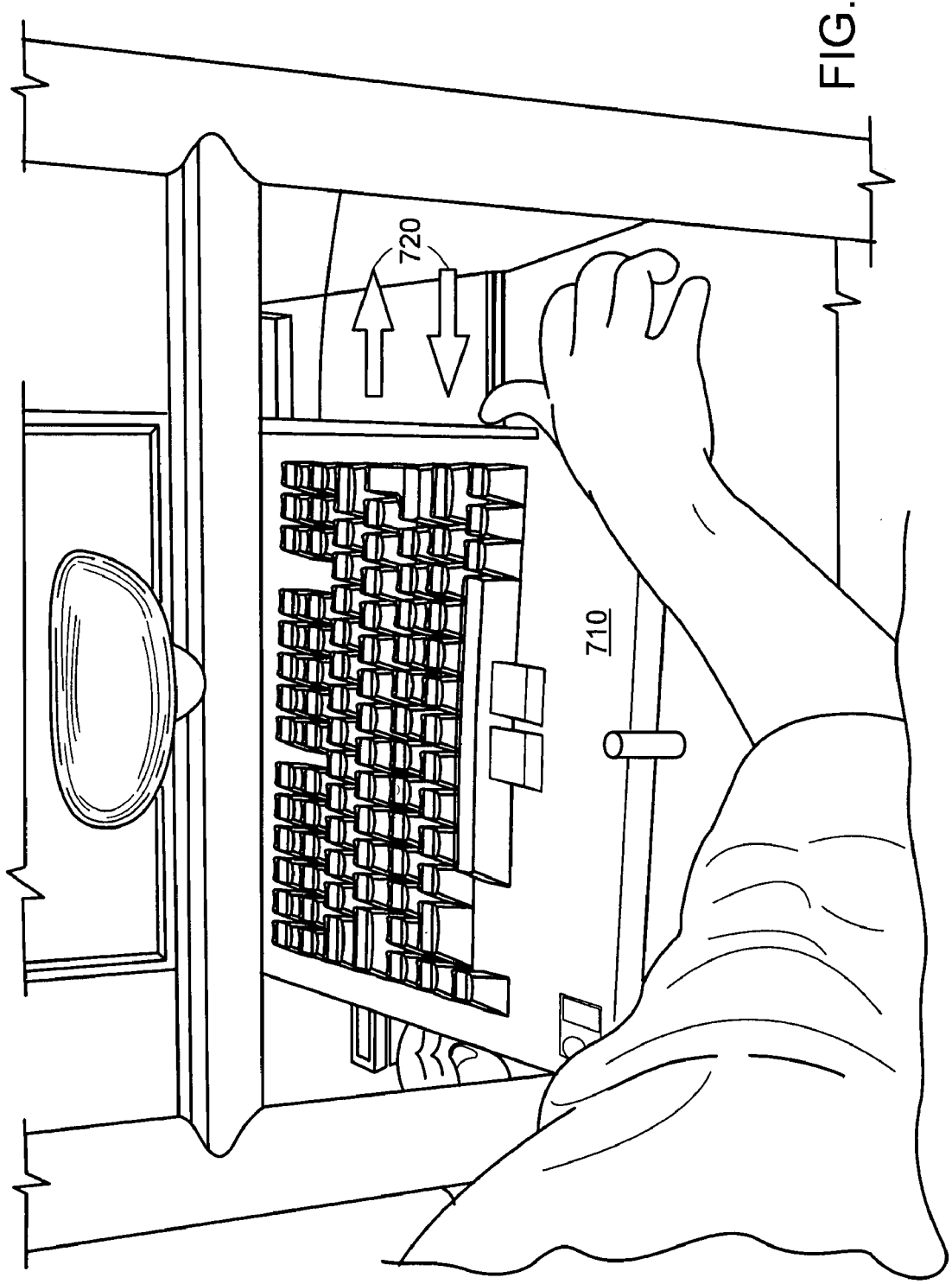
FIG. 7 depicts another view of the head-guide of FIG. 6 in which the position of the display may be adjusted in the horizontal direction in accord with an embodiment of the invention.

FIG. 6 depicts another related embodiment of the invention. Like FIG. 5B, the head-guide utilizes stop pins 670 to position the portable computer and display. The head-support, however, includes a molded chin rest 621 which is attached to the chin support bar 620. The chin support bar 620 is capable of sliding up and down between posts 611 having predetermined height adjustment settings 623. As depicted in FIG. 7, the portable computer 710 rests on a polycarbonate shelf (covered by the computer). The portable computer 710 may be positioned in the side-to-side direction 720 to horizontally align the fixation point of the user with a portion of the display of the portable computer 710. Predetermined markings on the display-support demark where a user slides the portable computer 710 such that the horizontal placement of the fixation point is determined. Such horizontal adjustment may also be performed by an appropriately configured head-support. As shown in FIG. 5A, head-support 510 has multiple chin rest positions 521 for changing the horizontal fixation point of a user in a predetermined manner.

In some embodiments of the invention, the vertical alignment of the fixation point of the user with the display is controlled by the head support (e.g., adjusting the height of a chin rest as depicted in FIG. 2). Alternatively, other embodiments of the invention may configure the display-support to allow vertical adjustment of the position of the display. For example, as shown in FIG. 2, the choice of which deck supports 261, 262 are used adjusts the height of the display. As is apparent to those skilled in the art, any number of ways of adjusting the height of the display may be utilized.

In another embodiment of the invention, a device for training vision of a user includes a head-guide and a CPU in communication with a display to be mounted in the head-guide. The CPU generates the visual stimuli presented by the display. The generation of the visual stimuli depends in part upon the pre-configuration of the head-support and display-support of the head-guide. Since the relative position of the head of a user and the display will dictate what portions of the display are in the visual field of the user, such information allows the CPU to generate visual stimuli in the appropriate portions of the display to train the user's vision. This may be of particular relevance in specifically training particular zones of a user's visual field.

Since various embodiments of head-guides may allow a number of pre-configured positions to be selected for the head-support and display-support, a CPU may be configured to produce any of a set of visual stimuli, each member of the set corresponding with a particular pre-configured position of the head-support, the display-support, or both. The set of visual stimuli may allow an individual user to obtain the appropriate visual stimuli for a training routine given a particular head-guide configuration without needing to calibrate the display.

Though previous embodiments of the present invention described herein refer to devices and methods for therapeutic training of the vision of a subject, such methods and devices can also be applied to train the vision of a person without regard to therapeutic treatment or training subjects with impaired vision only. Head-guides, and methods of using head-guides, may be directed to non-therapeutic training applications. Head-guides may be especially useful where quick visual identification of targets is advantageous. Nonlimiting examples include training the vision of athletes (e.g. golfers) to improve hand-eye coordination or reaction time, training in military applications (e.g., helping subjects improve their capability and efficiency in identifying targets on screens of equipment), and training for airplane pilots.

Further embodiments of the invention are directed toward devices and methods that diagnose a condition of vision in a user before training the vision of the user. In one embodiment of the invention, the CPU of a computer may generate visual stimuli to be presented on a display for use in diagnosing a condition of vision in a user. The head-guide of a device may be particularly preconfigured to conduct this diagnostic task by orienting the head of a user and display in a particular relative orientation to perform the diagnostic task. The diagnostic performance may be used to generate the visual stimuli used to train a user subsequently, in accord with other embodiments of the invention described herein. The corresponding methods including performing a diagnosis before conducting the training are within the scope of the present invention.

As well, embodiments of the invention may also incorporate existing designs of chin rests and head stabilizers, not described within this application, as part of a head-guide. Such chin rests and head stabilizers may typically be used as a table-mounted device without regard for a particular orientation of a head relative to a display. However, when associated with a display-support and guide-support in a manner to preconfigure the position of a head relative to a display for training or diagnostic purposes, the existing chin rests and head stabilizers may be part of a head-guide within the scope of the present invention.

All aforementioned embodiments of the invention are intended to be merely exemplary and numerous variations and modifications will be apparent to those skilled in the art. All such variations and modifications are intended to be within the scope of the present invention as defined in the appended claims.

What is claimed is:

1. A head-guide for diagnosing or treating vision of a user comprising:
   a head-support for orienting a head of the user, the head support including a chinrest,
   a display-support for orienting a display;
   a guide-support connected to the head-support and the display-support; and
   a CPU in communication with the display, the CPU generating the visual stimuli presented by the display, the CPU configured to generate the visual stimuli based upon a pre-configuration of the display-support and a pre-configuration of the head-support,
   wherein the head-support and display-support are pre-configured to fix the relative position of the head and the display, the display presenting visual stimuli to diagnose or treat the vision of the user.

2. A head-guide according to claim 1, wherein the head-support and display-support are configured to present a selected range of fixation points to the user.

3. A head-guide according to claim 1, wherein the head-support includes a head strap for supporting a forehead of the user.

4. A head-guide according to claim 1, wherein the head-support is configured to support the head of the user in a discrete number of preselected positions.

5. A head-guide according to claim 1, wherein the guide-support includes a base attached to the head-support and the display-support.

6. A head-guide according to claim 1, wherein the display-support is configured to support a preselected portable computer.

7. A head-guide according to claim 6, wherein the display-support includes a display base for positioning the portable computer in any of a discrete number of preselected positions.

8. A head-guide according to claim 1, wherein the display-support is configured to support the display in a discrete number of preselected positions.

9. A head-guide according to claim 1, wherein the head-guide is portable.

10. A head-guide according to claim 1, wherein the head-support and display-support are configured to present optical stimuli to a zone within the intact visual field of the user and to a zone outside the intact visual field of the user, and to treat vision in one of the zones.

11. A device according to claim 1, wherein the CPU is configured to generate the visual stimuli based upon a plurality of pre-configurations for at least one of the display-support and the head-support.

12. A device according to claim 1, wherein the CPU is configured to generate the visual stimuli for diagnosing a visual condition of the subject.

13. A device according to claim 1, wherein the visual stimuli are configured to therapeutically treat the vision of the subject.

14. A device according to claim 13, wherein the therapeutic treatment is designed to compensate for impairment of vision in the subject.

15. A head-guide for diagnosing or treating vision of a user comprising:
   a head-support for orienting a head of the user, the head support including a head strap for supporting a forehead of the user;
   a display-support for orienting a display that presents visual stimuli to diagnose or train the vision of the user;
   a guide-support connected to the head-support and the display-support; and
   a CPU in communication with the display, the CPU generating the visual stimuli presented by the display, the CPU configured to generate the visual stimuli based upon a pre-configuration of the display-support and a pre-configuration of the head-support,
   wherein the head-support and display-support are pre-configured to fix the relative position of the head and the display.

16. A head-guide according to claim 15, wherein the head support further comprises a chinrest.

17. A head-guide according to claim 15, wherein the head-support is configured to support the head of the user in a discrete number of preselected positions.

18. A head-guide according to claim 15, wherein the guide-support includes a base attached to the head-support and the display-support.

19. A head-guide according to claim 15, wherein the display-support is configured to support a preselected portable computer.

20. A head-guide according to claim 15, wherein the display-support includes a display base for positioning the portable computer in any of a discrete number of preselected positions.

21. A head-guide according to claim 15, wherein the display-support is configured to support the display in a discrete number of preselected positions.

22. A head-guide according to claim 15, wherein the head-guide is portable.

23. A head-guide according to claim 15, wherein the head-support and display-support are configured to present optical stimuli to a zone within the intact visual field of the user and to a zone outside the intact visual field of the user, and to treat vision in one of the zones.

24. A device according to claim 15, wherein the visual stimuli is configured to therapeutically treat the vision of the subject.

25. A device according to claim 15, wherein the CPU is configured to generate the visual stimuli based upon a plurality of pre-configurations for at least one of the display-support and the head-support.

26. A device according to claim 15, wherein the CPU is configured to generate the visual stimuli for diagnosing a visual condition of the subject.

27. A device according to claim 26, wherein the therapeutic treatment is designed to compensate for impairment of vision in the subject.

28. A head-guide for diagnosing or treating vision of a user comprising:
 a head-support for orienting a head of the user,
 a display-support for orienting a display;
 a guide-support connected to the head-support and the display-support;
wherein the head-support and display-support are pre-configured to fix the relative position of the head and the display, the display presenting visual stimuli to diagnose or treat the vision of the user; and
 a CPU in communication with the display, the CPU generating the visual stimuli presented by the display, the CPU configured to generate the visual stimuli based upon a pre-configuration of the display-support and a pre-configuration of the head-support.

29. A head guide according to claim 28, wherein the head support further comprises a head strap for supporting a forehead of the user.

30. A head guide according to claim 28, wherein the head support further comprises a chinrest.

31. A head-guide according to claim 28, wherein the head-support and display-support are configured to present a selected range of fixation points to the user.

32. A head-guide according to claim 28, wherein the head-support includes a head strap for supporting a forehead of the user.

33. A head-guide according to claim 28, wherein the head-support is configured to support the head of the user in a discrete number of preselected positions.

34. A head-guide according to claim 28, wherein the guide-support includes a base attached to the head-support and the display-support.

35. A head-guide according to claim 28, wherein the display-support is configured to support a preselected portable computer.

36. A head-guide according to claim 28, wherein the display-support includes a display base for positioning the portable computer in any of a discrete number of preselected positions.

37. A head-guide according to claim 28, wherein the display-support is configured to support the display in a discrete number of preselected positions.

38. A head-guide according to claim 28, wherein the head-guide is portable.

39. A head-guide according to claim 28, wherein the head-support and display-support are configured to present optical stimuli to a zone within the intact visual field of the user and to a zone outside the intact visual field of the user, and to treat vision in one of the zones.

40. A head-guide according to claim 28 wherein the CPU is configured to generate the visual stimuli based upon a plurality of pre-configurations for at least one of the display-support and the head-support.

41. A head-guide according to claim 28, wherein the CPU is configured to generate the visual stimuli for diagnosing a visual condition of the subject.

42. A head-guide according to claim 28 wherein the visual stimuli are configured to therapeutically treat the vision of the subject.

43. A head-guide according to claim 28, wherein the therapeutic treatment is designed to compensate for impairment of vision in the subject.

* * * * *

UNITED STATES PATENT AND TRADEMARK OFFICE
CERTIFICATE OF CORRECTION

| | | |
|---|---|---|
| PATENT NO. | : 7,642,990 B2 | Page 1 of 1 |
| APPLICATION NO. | : 11/153250 | |
| DATED | : January 5, 2010 | |
| INVENTOR(S) | : Todd et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1113 days.

Signed and Sealed this

Sixteenth Day of November, 2010

David J. Kappos
*Director of the United States Patent and Trademark Office*